(12) United States Patent
Lu et al.

(10) Patent No.: US 7,927,327 B2
(45) Date of Patent: Apr. 19, 2011

(54) MEDICAL INSTRUMENT HAVING AN ARTICULATABLE END EFFECTOR

(75) Inventors: Ifung Lu, Skokie, IL (US); Rudolph H. Nobis, Mason, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1128 days.

(21) Appl. No.: 11/411,214

(22) Filed: Apr. 25, 2006

(65) Prior Publication Data

US 2007/0250111 A1 Oct. 25, 2007

(51) Int. Cl.
*A61B 17/00* (2006.01)
(52) U.S. Cl. .......................... 606/1; 606/205
(58) Field of Classification Search .................. 606/1
See application file for complete search history.

(56) References Cited

U.S. PATENT DOCUMENTS

| 2,976,865 | A | 3/1961 | Shipley |
|---|---|---|---|
| 3,470,876 | A | 10/1969 | Barchilon |
| 3,521,620 | A | 7/1970 | Cook |
| 3,791,387 | A | 2/1974 | Itoh |
| 3,799,151 | A | 3/1974 | Fakaumi et al. |
| 3,805,791 | A | 4/1974 | Seuberth et al. |
| 4,102,478 | A | 7/1978 | Samoilov |
| 4,326,530 | A | 4/1982 | Fleury, Jr. |
| 4,493,320 | A | 1/1985 | Treat |
| 4,619,247 | A | 10/1986 | Inoue et al. |
| 4,638,802 | A | 1/1987 | Okada |
| 4,735,194 | A | 4/1988 | Stiegmann |
| 4,739,768 | A | 4/1988 | Engelson |
| 4,758,750 | A | 7/1988 | Itagaki et al. |
| 4,791,963 | A * | 12/1988 | Gronert et al. ................ 138/110 |
| 4,884,557 | A | 12/1989 | Takehana et al. |
| 4,890,602 | A | 1/1990 | Hake |
| 4,893,613 | A | 1/1990 | Hake |
| 4,930,494 | A | 6/1990 | Takehana et al. |
| 4,963,147 | A | 10/1990 | Agee et al. |
| 5,002,041 | A | 3/1991 | Chikama |

(Continued)

FOREIGN PATENT DOCUMENTS

DE 4408730 9/1995

(Continued)

OTHER PUBLICATIONS

Examination Report, European Application No. 07251728.7 (Dec. 17, 2008).

(Continued)

*Primary Examiner* — Henry M Johnson, III
*Assistant Examiner* — Jeffrey B Lipitz
(74) *Attorney, Agent, or Firm* — Victor C. Moreno

(57) ABSTRACT

A medical instrument includes a flexible tube, a distal member, a flexible end-effector activation wire, a proximal member, and a flexible first cable. The distal member is connected to the distal tube portion. The activation wire is positioned within the tube. The proximal member is attached to the tube. The first cable is positioned outside the tube, is substantially transversely constrained by the proximal member, and has a first distal cable portion attached to the distal member. Lengthwise translation of the first cable articulates the distal member with respect to the proximal member. Another instrument includes a drive screw which articulates an end effector (e.g., a grasper) pivotally connected to a tube. An additional instrument includes a drive screw which articulates a distal medical instrument member pivotally connected to a tube. A medical end effector (e.g., a snare) is positionable in a lumen of the distal medical instrument member.

18 Claims, 10 Drawing Sheets

U.S. PATENT DOCUMENTS

| | | |
|---|---|---|
| 5,035,696 A | 7/1991 | Rydell |
| 5,066,295 A | 11/1991 | Kozak et al. |
| 5,078,716 A | 1/1992 | Doll |
| 5,171,314 A | 12/1992 | Dulebohn |
| 5,201,732 A | 4/1993 | Parins et al. |
| 5,201,741 A | 4/1993 | Dulebohn |
| 5,250,060 A | 10/1993 | Carbo et al. |
| 5,293,869 A | 3/1994 | Edwards et al. |
| 5,322,505 A | 6/1994 | Krause et al. |
| 5,342,299 A | 8/1994 | Snoke et al. |
| 5,346,504 A | 9/1994 | Ortiz et al. |
| 5,351,692 A | 10/1994 | Dow et al. |
| 5,353,807 A | 10/1994 | DeMarco |
| 5,397,304 A | 3/1995 | Truckai |
| 5,409,453 A | 4/1995 | Lundquist et al. |
| 5,431,671 A | 7/1995 | Nallakrishnan |
| 5,433,721 A | 7/1995 | Hooven et al. |
| 5,441,499 A | 8/1995 | Fritzsch |
| 5,482,029 A | 1/1996 | Sekiguchi et al. |
| 5,522,829 A | 6/1996 | Michalos |
| 5,531,664 A | 7/1996 | Adachi et al. |
| 5,531,686 A | 7/1996 | Lundquist et al. |
| 5,542,948 A | 8/1996 | Weaver et al. |
| 5,618,294 A | 4/1997 | Aust et al. |
| 5,628,719 A | 5/1997 | Hastings et al. |
| 5,706,827 A | 1/1998 | Ehr et al. |
| 5,728,044 A | 3/1998 | Shan |
| 5,749,828 A | 5/1998 | Solomon et al. |
| 5,752,961 A | 5/1998 | Hill |
| 5,776,080 A | 7/1998 | Thome et al. |
| 5,792,165 A | 8/1998 | Klieman et al. |
| 5,810,715 A | 9/1998 | Moriyama |
| 5,810,807 A | 9/1998 | Ganz et al. |
| 5,836,947 A | 11/1998 | Fleischman |
| 5,848,986 A | 12/1998 | Lundquist et al. |
| 5,865,724 A | 2/1999 | Palmer et al. |
| 5,897,554 A | 4/1999 | Chia et al. |
| 5,972,012 A | 10/1999 | Ream et al. |
| 6,066,102 A | 5/2000 | Townsend et al. |
| 6,071,277 A | 6/2000 | Farley et al. |
| 6,074,408 A | 6/2000 | Freeman |
| 6,093,185 A | 7/2000 | Ellis et al. |
| 6,093,195 A | 7/2000 | Ouchi |
| 6,152,918 A | 11/2000 | Padilla et al. |
| 6,174,280 B1 | 1/2001 | Oneda et al. |
| 6,203,494 B1 | 3/2001 | Moriyama |
| 6,352,503 B1 | 3/2002 | Matsui et al. |
| 6,371,907 B1 | 4/2002 | Hasegawa et al. |
| 6,395,001 B1 | 5/2002 | Ellman et al. |
| 6,423,059 B1 | 7/2002 | Hanson et al. |
| 6,443,943 B1 | 9/2002 | Ouchi |
| 6,443,944 B1 | 9/2002 | Doshi et al. |
| 6,450,948 B1 | 9/2002 | Matsuura et al. |
| 6,451,014 B1 | 9/2002 | Wakikaido et al. |
| 6,454,703 B1 | 9/2002 | Ide |
| 6,454,758 B1 | 9/2002 | Thompson |
| 6,475,222 B1 | 11/2002 | Berg et al. |
| 6,482,149 B1 | 11/2002 | Torii |
| 6,488,658 B1 | 12/2002 | Long |
| 6,500,189 B1 | 12/2002 | Lang et al. |
| 6,569,105 B1 | 5/2003 | Kortenbach et al. |
| 6,579,300 B2 | 6/2003 | Griego et al. |
| 6,602,267 B2 | 8/2003 | Castaneda |
| 6,612,992 B1 | 9/2003 | Hossack et al. |
| 6,663,616 B1 | 12/2003 | Roth et al. |
| 6,663,625 B1 | 12/2003 | Ormsby et al. |
| 6,709,388 B1 | 3/2004 | Mosse et al. |
| 6,730,097 B2 | 5/2004 | Dennis |
| 6,743,240 B2 | 6/2004 | Smith et al. |
| 6,764,441 B2 | 7/2004 | Chiel et al. |
| 6,866,626 B2 | 3/2005 | Long et al. |
| 7,060,024 B2 | 6/2006 | Long et al. |
| 7,060,025 B2 | 6/2006 | Long et al. |
| 7,066,879 B2 | 6/2006 | Fowler et al. |
| 7,093,518 B2 | 8/2006 | Gmeilbauer |
| 7,118,587 B2 | 10/2006 | Dycus et al. |
| 2001/0029397 A1 | 10/2001 | Thompson |
| 2001/0037084 A1 | 11/2001 | Nardeo |
| 2002/0017515 A1 | 2/2002 | Obata et al. |
| 2002/0087208 A1 | 7/2002 | Koblish et al. |
| 2002/0095168 A1 | 7/2002 | Griego et al. |
| 2002/0120178 A1 | 8/2002 | Tartaglia et al. |
| 2002/0147445 A1 | 10/2002 | Farley et al. |
| 2002/0177802 A1 | 11/2002 | Moutafis et al. |
| 2003/0014051 A1 | 1/2003 | Woloszko |
| 2003/0032863 A1 | 2/2003 | Kazakevich |
| 2003/0045778 A1 | 3/2003 | Ohline et al. |
| 2003/0074014 A1 | 4/2003 | Castaneda |
| 2003/0109898 A1 | 6/2003 | Schwartz et al. |
| 2003/0125788 A1 | 7/2003 | Long |
| 2003/0153866 A1 | 8/2003 | Long et al. |
| 2003/0181785 A1 | 9/2003 | Viebach et al. |
| 2003/0195492 A1 | 10/2003 | Gobron et al. |
| 2003/0208219 A1 | 11/2003 | Aznoian et al. |
| 2004/0034343 A1 | 2/2004 | Gillespie et al. |
| 2004/0044350 A1 | 3/2004 | Martin et al. |
| 2004/0068291 A1 | 4/2004 | Suzuki |
| 2004/0092953 A1 | 5/2004 | Salameh et al. |
| 2004/0097919 A1 | 5/2004 | Wellman et al. |
| 2004/0143159 A1 | 7/2004 | Wendlandt |
| 2004/0143160 A1 | 7/2004 | Couvillon, Jr. |
| 2004/0193016 A1 | 9/2004 | Root et al. |
| 2004/0204645 A1 | 10/2004 | Saadat et al. |
| 2004/0230096 A1 | 11/2004 | Stefanchik et al. |
| 2005/0043743 A1 | 2/2005 | Dennis |
| 2005/0183733 A1 | 8/2005 | Kawano et al. |
| 2005/0203610 A1 | 9/2005 | Tzeng |
| 2005/0222587 A1 | 10/2005 | Jinno et al. |
| 2005/0234296 A1 | 10/2005 | Saadat et al. |
| 2005/0272975 A1 | 12/2005 | McWeeney et al. |
| 2005/0273084 A1* | 12/2005 | Hinman et al. .................. 606/1 |
| 2005/0273085 A1 | 12/2005 | Hinman et al. |
| 2006/0009711 A1 | 1/2006 | Gingrich et al. |
| 2006/0089627 A1 | 4/2006 | Burnett et al. |
| 2007/0225562 A1 | 9/2007 | Spivey et al. |

FOREIGN PATENT DOCUMENTS

| | | |
|---|---|---|
| DE | 19729499 | 1/1999 |
| EP | 0027704 | 4/1981 |
| EP | 0397489 | 11/1990 |
| EP | 1310206 | 5/2003 |
| EP | 1849421 | 10/2007 |
| JP | 59-181124 | 10/1984 |
| JP | 2004-154164 | 6/2004 |
| WO | WO 96/00030 | 1/1996 |
| WO | 96/10957 | 4/1996 |
| WO | WO 97/12557 | 4/1997 |
| WO | 97/35135 | 9/1997 |
| WO | 99/12489 | 3/1999 |
| WO | 01/08737 | 2/2001 |
| WO | 01/82814 | 11/2001 |
| WO | 01/93938 | 12/2001 |
| WO | 02/43797 | 6/2002 |
| WO | 03/053225 | 7/2003 |
| WO | 03/092476 | 11/2003 |
| WO | 2005/113051 | 12/2005 |
| WO | 2006/019291 | 2/2006 |
| WO | 2006/026687 | 3/2006 |
| WO | 2006/122279 | 11/2006 |

OTHER PUBLICATIONS

Ginsberg, G.G., "Colonoscopy with the variable stiffness colonoscope," Gastrointestinal Endoscopy, vol. 58, No. 4 (2003).

Brooker, J.C. et al., "A new variable stiffness colonoscope makes colonoscopy easier: a randomised controlled trial," Gut 2000, 46, pp. 801-805 (2000).

Rex, D.K., "Effect of Variable Stiffness Colonoscopes on Cecal Intubation Times for Routine Colonoscopy by an Experienced Examiner in Sedated Patients," EndoscopY; 33 (1), pp. 60-64 (2001).

Shah, S.G., et al., "Magnetic imaging of colonoscopy: an audit of looping, accuracy and ancillary maneuvers," Gastrointestinal Endoscopy, vol. 52, No. 1, pp. 1-8 (2000).

Shah, S.G., et al., "The variable stiffness colonoscope: assessment of efficacy by magnetic endoscope imaging," Gastrointestinal Endoscopy, vol. 56, No. 2, pp. 195-201 (2002).

"Sensors-Resistance," Smart Engineering Group (1999).

European Search Report, European Application No. 07251934 (2 pages) (dated Aug. 30, 2007).

CN, Office Action, Chinese Application No. 200710104701.X (Mar. 12, 2010).

EP, Partial Search Report, European Application No. 07251728.7 (Feb. 19, 2008).

EP, Search Report, European Application No. 07251728.7 (May 8, 2008).

* cited by examiner

MEDICAL INSTRUMENT HAVING AN ARTICULATABLE END EFFECTOR

FIELD OF THE INVENTION

The present invention is related generally to medical equipment, and more particularly to a medical instrument having an articulatable end effector.

BACKGROUND OF THE INVENTION

Endoscopes (including colonoscopes) are known which have an insertion tube which is insertable within a patient. The insertion tube has an articulatable distal end portion controlled by wires running from the distal end portion to control knobs on the handle of the endoscope. A wide angle video camera in the distal end of the insertion tube permits medical observation. Medical devices, such as a medical snare, are part of an endoscopic system and are insertable into the working channel(s) of the insertion tube of the endoscope and are translatable to extend from the distal end portion for medical treatment. Other medical devices are known which use a pull wire to articulate an end effector about a pivot pin.

Still, scientists and engineers continue to seek improved medical instruments having an articulatable end effector.

SUMMARY OF THE INVENTION

A first expression of a first embodiment of the invention is for a medical instrument including a flexible tube, a medical end effector, a flexible medical-end-effector activation wire, a proximal medical instrument member, and a flexible, lengthwise-translatable first cable. The flexible tube has a distal tube portion insertable within a patient. The medical end effector is connected to the distal tube portion. The medical-end-effector activation wire is positioned within the tube. The proximal medical instrument member is spaced apart from, and is positioned proximal to, the medical end effector. The proximal medical instrument member is attached to the tube. The lengthwise-translatable first cable is positioned outside the tube, is substantially transversely constrained by the proximal medical instrument member, and has a first distal cable portion attached to the medical end effector. Lengthwise translation of the first cable articulates the medical end effector with respect to the proximal medical instrument member.

A first expression of a second embodiment of the invention is for a medical instrument including a flexible tube, a distal medical instrument member, a medical end effector, a flexible activation wire, a proximal medical instrument member, and a flexible, lengthwise-translatable first cable. The flexible tube defines a passageway and has a distal tube portion insertable within a patient. The distal medical instrument member is connected to the distal tube portion and has a lumen in communication with the passageway. The medical end effector is positionable in the lumen of the distal medical instrument member. The activation wire is positionable in the passageway and is connected to the medical end effector. The proximal medical instrument member is spaced apart from, and positioned proximal to, the distal medical instrument member, wherein the proximal medical instrument member is attached to the tube. The lengthwise-translatable first cable is positioned outside the tube, is substantially transversely constrained by the proximal medical instrument member, and has a distal cable portion attached to the distal medical instrument member. Lengthwise translation of the first cable articulates the distal medical instrument member with respect to the proximal medical instrument member.

A first expression of a third embodiment of the invention is for a medical instrument including a tube, a medical end effector, a drive screw, a sled, and a linkage. The tube has a distal tube end insertable within a patient. The medical end effector has a distal portion and a proximal portion. The proximal portion of the medical end effector is pivotally connected to the tube proximate the distal tube end. The drive screw is positioned in the tube proximal the proximal portion of the end effector. The sled is translatable by rotation of the drive screw. The linkage has a first end portion pivotally connected to the sled and has a second end portion pivotally connected to the medical end effector between the proximal and distal portions of the medical end effector. Rotation of the drive screw translates the sled moving the linkage to articulate the medical end effector with respect to the distal tube end.

A first expression of a fourth embodiment of the invention is for a medical instrument including a tube, a distal medical instrument member, a medical end effector, an activation wire, a drive screw, a sled, and a linkage. The tube defines a passageway and has a distal tube end insertable within a patient. The distal medical instrument member has a proximal end portion pivotally connected to the distal tube portion and has a lumen in communication with the passageway. The medical end effector is positionable in the lumen of the distal medical instrument member. The activation wire is positionable in the passageway and is connected to the medical end effector. The drive screw is positioned in the tube proximal the distal medical instrument member. The sled is translatable by rotation of the drive screw. The linkage has a first end portion pivotally connected to the sled and has a second end portion pivotally connected to the distal medical instrument member distal the proximal end portion of the distal medical instrument member. Rotation of the drive screw translates the sled moving the linkage to articulate the distal medical instrument member with respect to the distal tube portion.

A first expression of a fifth embodiment of the invention is for a medical instrument including a flexible tube, a distal medical instrument member, a flexible medical-end-effector activation wire, a proximal medical instrument member, and a flexible, lengthwise-translatable first cable. The flexible tube has a distal tube portion insertable within a patient. The distal medical instrument member is connected to the distal tube portion. The medical-end-effector activation wire is positioned within the tube. The proximal medical instrument member is spaced apart from, and is positioned proximal to, the distal medical instrument member. The proximal medical instrument member is attached to the tube. The lengthwise-translatable first cable is positioned outside the tube, is substantially transversely constrained by the proximal medical instrument member, and has a first distal cable portion attached to the distal medical instrument member. Lengthwise translation of the first cable articulates the distal medical instrument member with respect to the proximal medical instrument member.

Several benefits and advantages are obtained from one or more of the expressions of the embodiments of the invention. In a first example of the first expression of the first, second, third and/or fourth embodiments, the tube is inserted into a working channel of a flexible insertion tube of an endoscope, wherein the medical end effector can be articulated with respect to the insertion tube of the endoscope allowing independent alignment of the wide angle video camera of the endoscope and the medical end effector. In a second example of the first expression of the first, second, third and/or fourth embodiments, the tube has a tube-to-endoscope-rail distal medical instrument member feature allowing the tube to be coupled to, and slid along, an exterior rail of a flexible insertion tube of an endoscope allowing independent alignment of the wide angle video camera of the endoscope and the medical end effector. The cable embodiments allow, with multiple cables, articulation which is not limited to a single plane. The drive screw embodiments allow pivotal articulation unhindered by tube bending from endoscopic insertion within a patient.

The present invention has, without limitation, application in hand-activated instruments as well as in robotic-assisted instruments.

DETAILED DESCRIPTION OF THE INVENTION

This application incorporates by reference the concurrently-filed and commonly-assigned U.S. patent application entitled "MEDICAL TUBULAR ASSEMBLY".

Before explaining the present invention in detail, it should be noted that the invention is not limited in its application or use to the details of construction and arrangement of parts illustrated in the accompanying drawings and description. The illustrative embodiments of the invention may be implemented or incorporated in other embodiments, variations and modifications, and may be practiced or carried out in various ways. Furthermore, unless otherwise indicated, the terms and expressions employed herein have been chosen for the purpose of describing the illustrative embodiments of the present invention for the convenience of the reader and are not for the purpose of limiting the invention.

It is understood that any one or more of the following-described embodiments, examples, etc. can be combined with any one or more of the other following-described embodiments, examples, etc.

Figure 1:
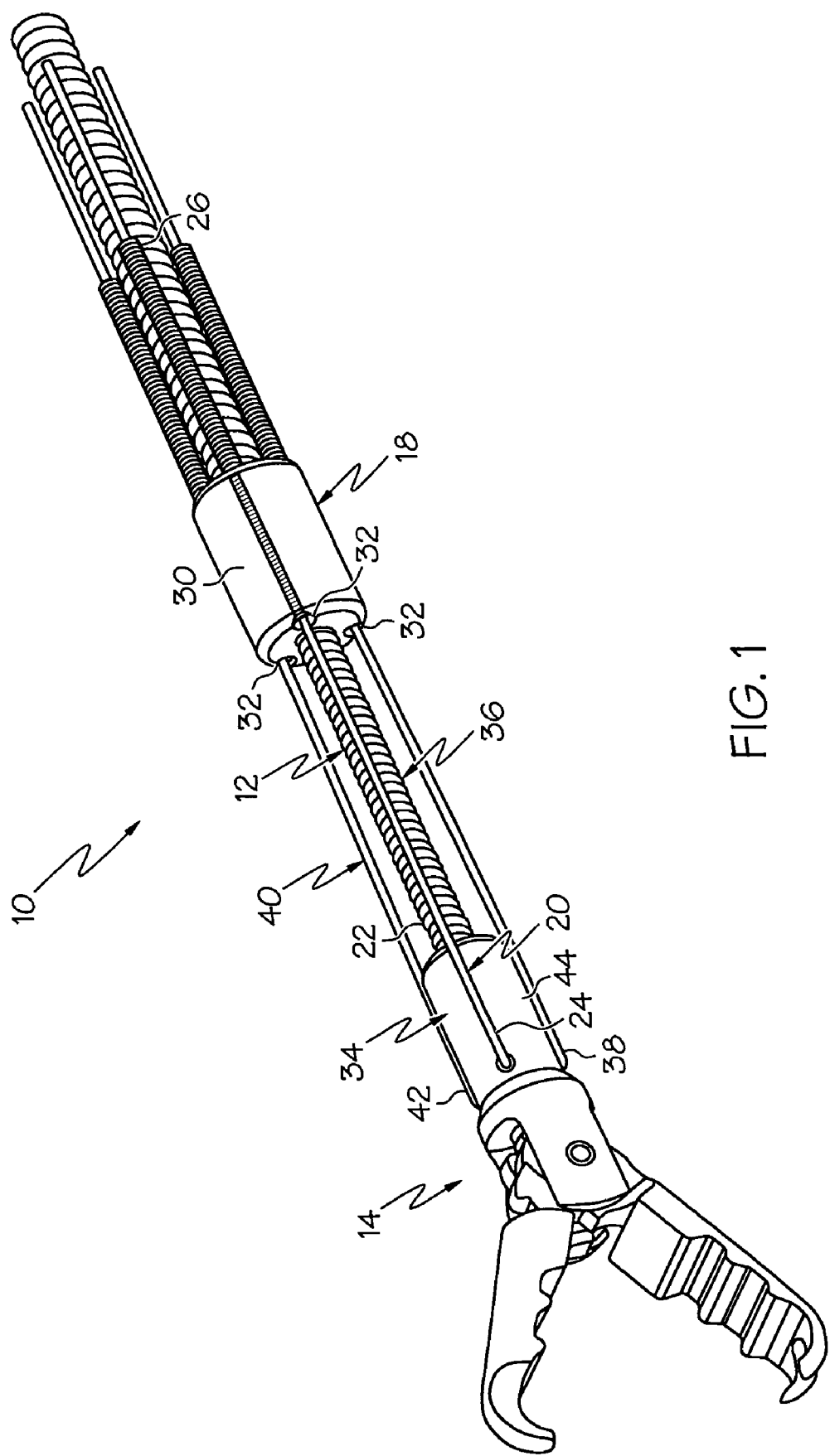
FIG. 1 is a schematic perspective view of a first embodiment of the medical instrument of the invention, wherein pulling of at least one cable articulates the medical end effector, and wherein the medical end effector is a medical grasper.
Figure 2:
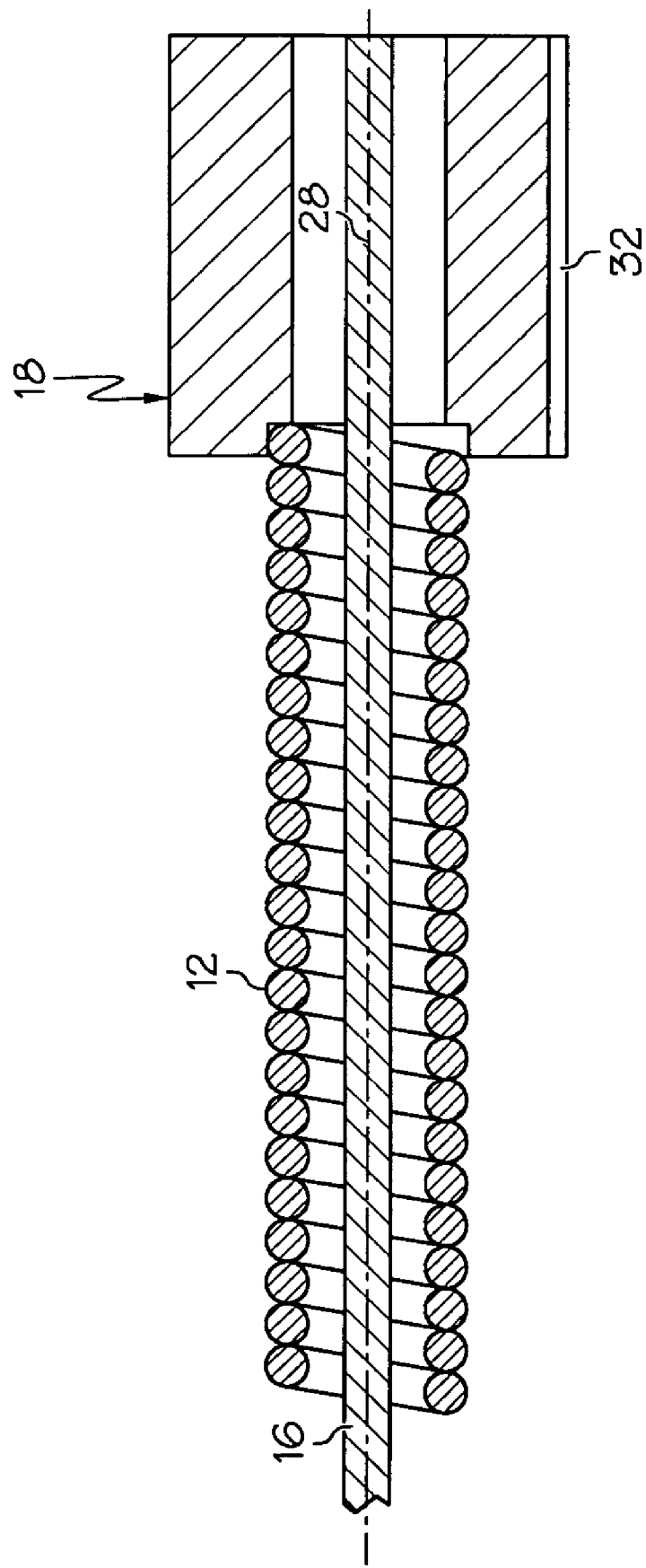
FIG. 2 is a side elevational, cross sectional view of the proximal medical instrument member and a portion of the tube of FIG. 1.

Referring now to the Figures, wherein like numerals represent like elements throughout, FIGS. 1-2 illustrate a first embodiment of the invention. A first expression of the embodiment of FIGS. 1-2 is for a medical instrument 10 including a flexible tube 12, a medical end effector 14, a flexible medical-end-effector activation wire 16, a proximal medical instrument member 18, and a flexible, lengthwise-translatable first cable 20. The flexible tube 12 has a distal tube portion 22 insertable within a patient. The medical end effector 14 is connected to the distal tube portion 22. The medical-end-effector activation wire 16 is disposed within the tube 12. The proximal medical instrument member 18 is spaced apart from, and is disposed proximal to, the medical end effector 14. The proximal medical instrument member 18 is attached to the tube 12. The lengthwise-translatable first cable 20 is disposed outside the tube 12, is substantially transversely constrained by the proximal medical instrument member 18, and has a distal cable portion 24 attached to the medical end effector 14. Lengthwise translation of the first cable 20 articulates the medical end effector 14 with respect to the proximal medical instrument member 18.

In one example, without limitation, of the first expression of the first embodiment of FIGS. 1-2, the proximal medical instrument member 18 is a fitting. It is noted that the term "cable" and the term "wire" include any elongated member. In one choice of materials, the activation wire 16 and the first cable 20 comprise, consist essentially of, or consist of nitinol.

In one enablement of the first expression of the first embodiment of FIGS. 1-2, pulling of the first cable 20 articulates the medical end effector 14 with respect to the proximal medical instrument member 18. In the same of a different enablement, pushing of the first cable 20 articulates the medical end effector 14 with respect to the proximal medical instrument member 18.

In one implementation of the first expression of the first embodiment of FIGS. 1-2, the medical instrument 10 also includes a flexible first pipe 26 surrounding the first cable 20 and attached to the proximal medical instrument member 18. In one variation, the first pipe 26 does not extend distally of the proximal medical instrument member 18. In the same or a different variation, the first pipe 26 is a first coil pipe. In the same or a different variation, the proximal medical instrument member 18 has a longitudinal axis 28, and the tube 12 is substantially coaxially aligned with the longitudinal axis 28 within the proximal medical instrument member 18. In one modification, the proximal medical instrument member 18 has a longitudinally-extending circumferential surface 30, and the first pipe 26 is disposed in a surface groove 32 (three grooves are shown in FIG. 1 and one groove is shown in FIG. 2) of the circumferential surface 30 of the proximal medical instrument member 18. In one example, the tube 12 is a coil-pipe tube. In a first employment, adjacent coil turns of a coil pipe are in contact with each other. In a second employment, adjacent coil turns of a coil pipe are spaced apart from each other.

In a first construction of the first expression of the first embodiment of FIGS. 1-2, the medical end effector 14 has a proximal end-effector portion 34, and the first cable 20 is attached to the proximal end-effector portion 34 of the medical end effector 14. In one variation, the proximal medical instrument member 18 has a first diameter, and the proximal end-effector portion 34 has a second diameter which is substantially equal to the first diameter. In the same or a different variation, the tube 12 has a diameter which is smaller than the first diameter distal of the proximal medical instrument member 18. In a first different variation, not shown, the second diameter is greater than the first diameter. In a second different variation, not shown, the second diameter is less than the first diameter.

In one configuration of the first expression of the first embodiment of FIGS. 1-2, the medical instrument 10 also includes a flexible, lengthwise-translatable second cable 36 disposed outside the tube 12, substantially transversely constrained by the proximal medical instrument member 18, and having a distal cable portion 38 attached to the medical end effector 14, wherein lengthwise translation of the second cable 36 articulates the medical end effector with respect to the proximal medical instrument member 18. In one variation, the medical instrument 10 also includes a flexible, lengthwise-translatable third cable 40 disposed outside the tube 12, substantially transversely constrained by the proximal medical instrument member 18, and having a distal cable portion 42 attached to the medical end effector 14, wherein lengthwise translation of the third cable 40 articulates the medical end effector 14 with respect to the proximal medical instrument member 18.

In one illustration, the medical end effector 14 has a proximal end-effector portion 34, and the first, second and third cables 20, 36 and 40 are attached to the proximal end-effector portion 34 of the medical end effector 14. In one modification, the proximal end-effector portion 34 has a circumferential surface 44, and the first, second and third cables 20, 36 and 40 are spaced apart from each other by substantially 120 degrees about the circumferential surface 44 of the proximal end-effector portion 34. In one deployment, pulling of the first, second and third cables 20, 36 and 40, either alone or in pairs articulates the medical end effector 14 with respect to the proximal medical instrument member 18.

Examples, without limitation, of medical end effectors 14 of the first expression of the embodiment of FIGS. 1-2, include a medical grasper (as shown in FIG. 1) and include medical forceps (not shown). Other examples are left to the artisan. In the example of the medical grasper, the activation wire 16 is operatively connected to the jaw opening and closing mechanism of the medical grasper as is well known in the art.

Figure 3:
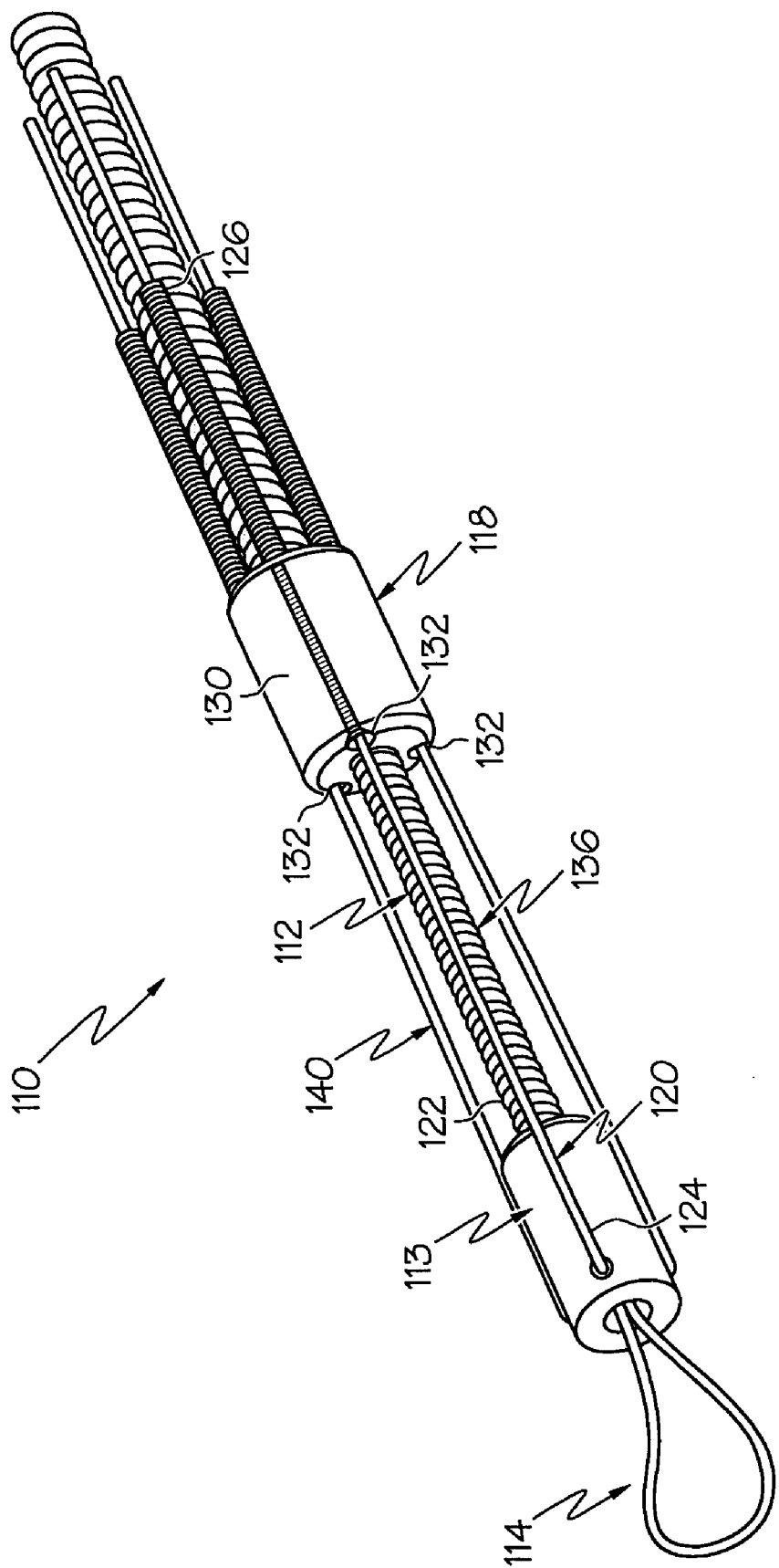
FIG. 3 is a schematic perspective view of a second embodiment of the medical instrument of the invention, wherein pulling of at least one cable articulates a distal medical instrument member which has a lumen in which a medical end effector is disposable, and wherein the medical end effector is a medical snare.
Figure 4:
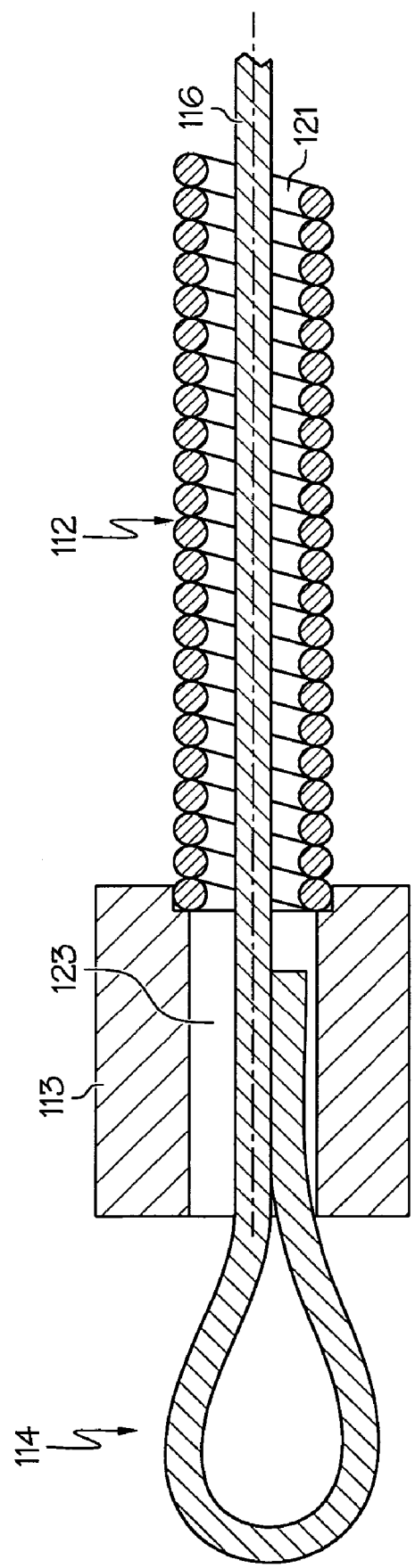
FIG. 4 is a side elevational, cross sectional view of the distal medical instrument member and a portion of the tube of FIG. 3.

A second embodiment of the invention is shown in FIGS. 3-4. A first expression of the second embodiment of FIGS. 3-4 is for a medical instrument 110 including a flexible tube 112, a distal medical instrument member 113, a medical end effector 114, a flexible activation wire 116, a proximal medical instrument member 118, and a flexible, lengthwise-translatable first cable 120. The flexible tube 112 defines a passageway 121 and has a distal tube portion 122 insertable within a patient. The distal medical instrument member 113 is connected to the distal tube portion 122 and has a lumen 123 in communication with the passageway 121. The medical end effector 114 is disposable in the lumen 123 of the distal medical instrument member 113. The activation wire 116 is disposable in the passageway 121 and is connected to the medical end effector 114. The proximal medical instrument member 118 is spaced apart from, and disposed proximal to, the distal medical instrument member 113, wherein the proximal medical instrument member 118 is attached to the tube 112. The lengthwise-translatable first cable 120 is disposed outside the tube 112, is substantially transversely constrained by the proximal medical instrument member 118, and has a distal cable portion 124 attached to the distal medical instrument member 113. Lengthwise translation of the first cable 120 articulates the distal medical instrument member 113 with respect to the proximal medical instrument member 118. In one example, without limitation, the proximal medical instrument member 118 is a fitting and the distal medical instrument member 113 is a coupling.

In one implementation of the first expression of the second embodiment of FIGS. 3-4, the medical instrument 110 also includes a flexible first pipe 126 surrounding the first cable 120 and attached to the proximal medical instrument member 118, wherein the proximal medical instrument member 118 has a longitudinally-extending circumferential surface 130, wherein the first pipe 126 is disposed in a surface groove 132 (three grooves are shown in FIG. 3) of the circumferential surface 130 of the proximal medical instrument member 118, and wherein the first pipe 126 does not extend distally of the proximal medical instrument member 118. In one variation, the first pipe 126 is a first coil pipe. In one example, the tube 112 is a coil-pipe tube. In one employment, the activation wire 116 is monolithically connected to the medical end effector 114. Thus, in this employment, the activation wire 116 and the medical end effector 114 are two portions of one continuous piece.

Examples, without limitation, of medical end effectors 114 of the first expression of the embodiment of FIGS. 3-4, include a medical snare (as shown in FIGS. 3-4) and include an electrocautery needle knife (not shown). Other examples are left to the artisan. In one example employing the medical snare, the first cable 120 articulates the distal medical instrument member 113 to a desired orientation, the activation wire 116 is pushed to extend the medical snare out of the distal end of the distal medical instrument member 113 and around patient tissue (such as a polyp), and the activation wire 116 is then pulled to excise the polyp and retract the medical snare (and polyp) into the distal end of the distal medical instrument member 113. In one configuration, the medical instrument 110 includes a flexible second cable 136 and a flexible third cable 140 as shown in FIG. 3.

Figure 5:
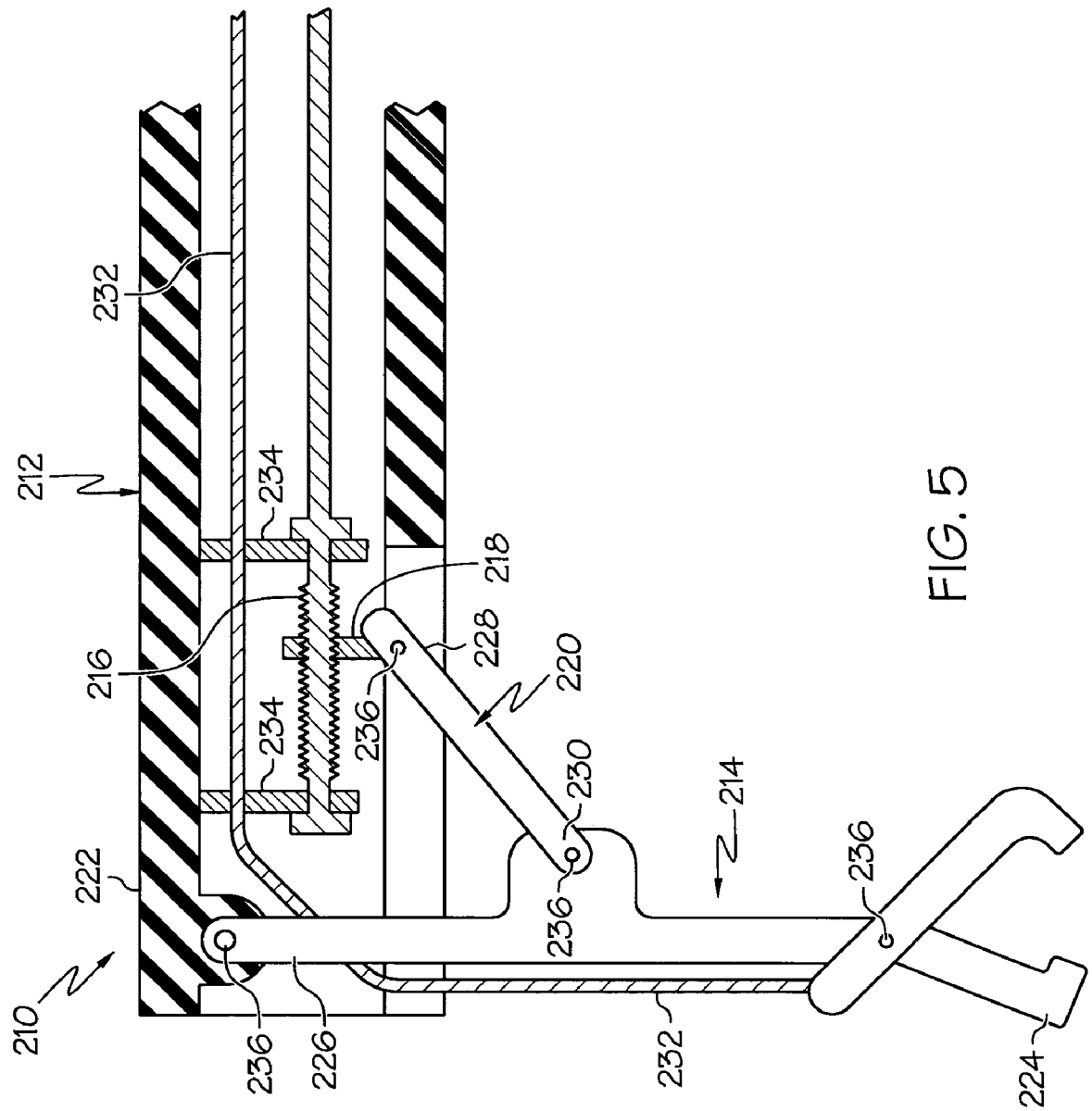
FIG. 5 is a schematic, side elevational, cross sectional view of a third embodiment of the medical instrument of the invention, wherein rotation of a drive screw is used to articulate the medical end effector, and wherein the medical end effector is a medical grasper.

A third embodiment of the invention is shown in FIG. 5. A first expression of the third embodiment of FIG. 5 is for a medical instrument 210 including a tube 212, a medical end effector 214, a drive screw 216, a sled 218, and a linkage 220. The tube 212 has a distal tube end 222 insertable within a patient. The medical end effector 214 has a distal portion 224 and a proximal portion 226. The proximal portion 226 of the medical end effector 214 is pivotally connected to the tube 212 proximate the distal tube end 222. The drive screw 216 is positioned in the tube 212 proximal the proximal portion 226 of the end effector 214. The sled 218 is translatable by rotation of the drive screw 216. The linkage 220 has a first end portion 228 pivotally connected to the sled 218 and has a second end portion 230 pivotally connected to the medical end effector 214 between the proximal and distal portions 226 and 224 of the medical end effector 214. Rotation of the drive screw 216 translates the sled 218 moving the linkage 220 to articulate the medical end effector 214 with respect to the distal tube end 222. In one arrangement, the sled 218 has internal threads engaging external threads on the drive screw 216. In one enablement, the tube 212 is a flexible tube.

Examples, without limitation, of medical end effectors 214 of the first expression of the embodiment of FIG. 5, include a medical grasper (as shown in FIG. 5) and include medical forceps (not shown). Other examples are left to the artisan. In the example of the medical grasper, an activation wire 232 is operatively connected to the jaw opening and closing mechanism of the medical grasper as is well known in the art. In one construction, bearing supports 234 for the drive screw 216 and pivot pins 236 for pivotal connections are provided as shown in FIG. 5, wherein the bearing supports 234 have channels for passage of the activation wire 232. Other constructions are left to the artisan.

Figure 6:
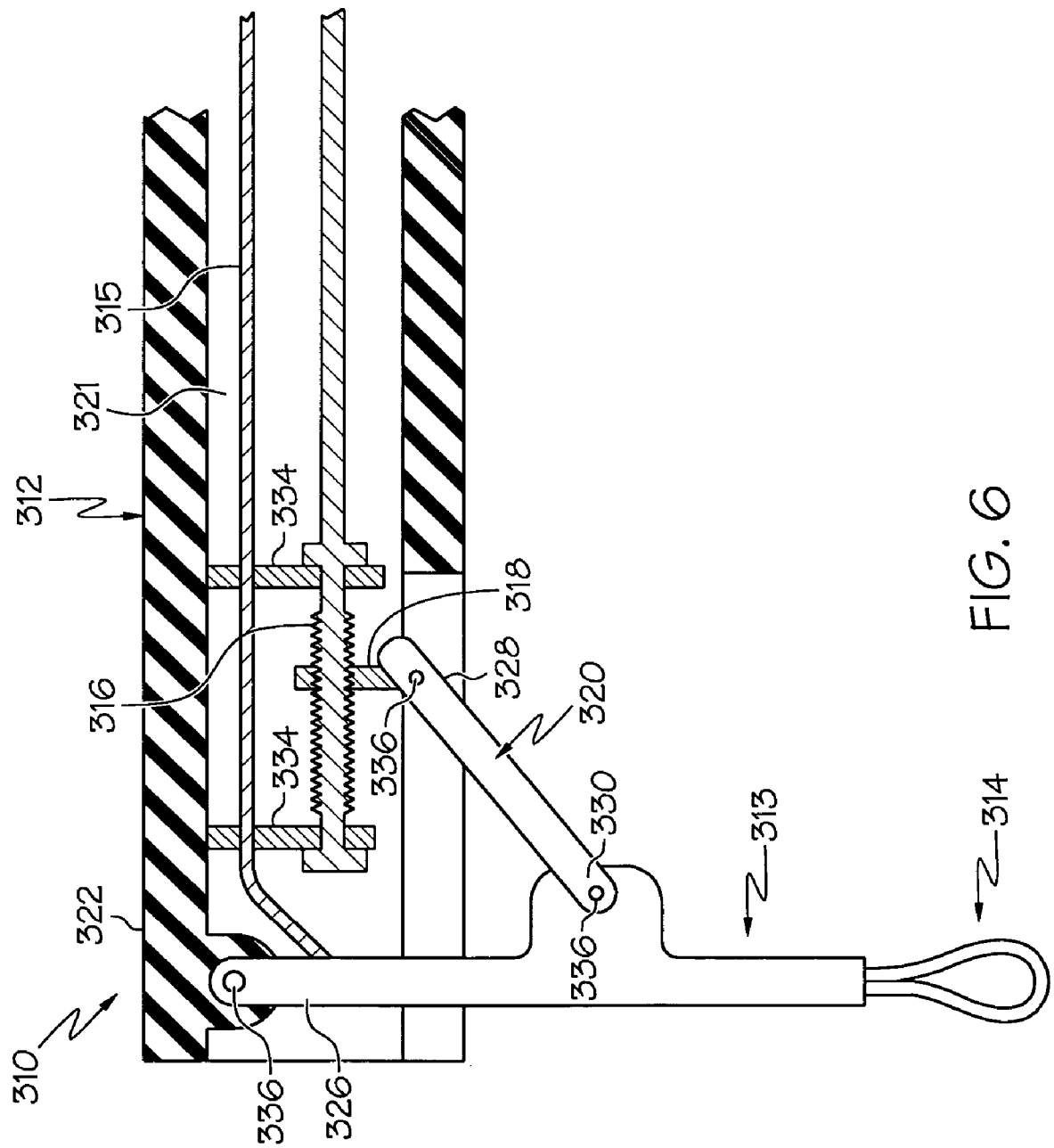
FIG. 6 is a schematic, side elevational, cross sectional view of a fourth embodiment of the medical instrument of the invention, wherein rotation of a drive screw is used to articulate a distal medical instrument member which has a lumen in which a medical end effector is disposable, and wherein the medical end effector is a medical snare.
Figure 7:
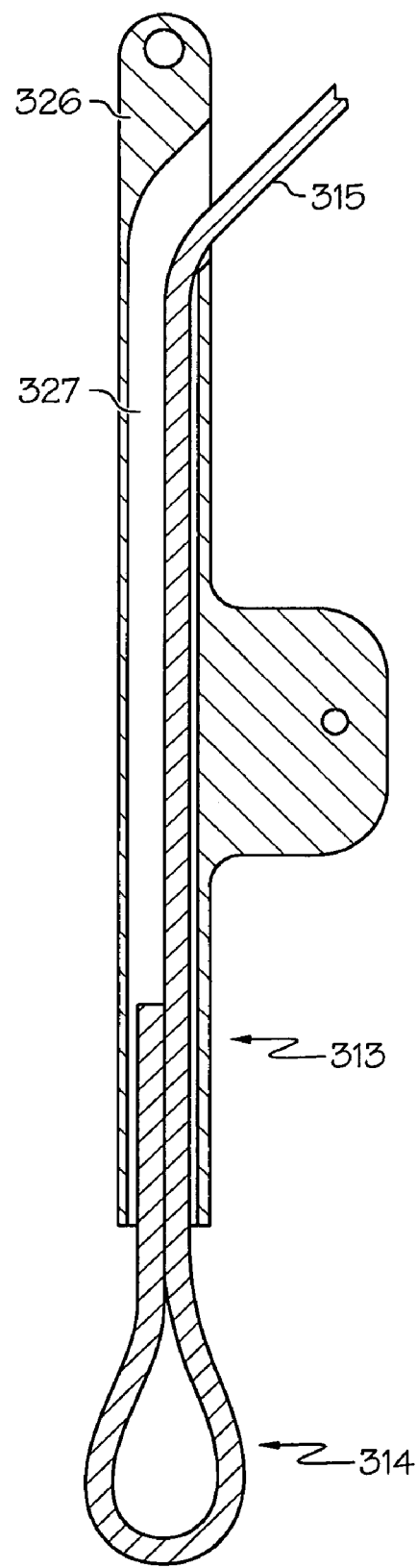
FIG. 7 is a side elevational, cross sectional view of the distal medical instrument member (with pivot pins removed) and the medical end effector of FIG. 6 and of the non-cross-sectioned portion and the hidden portion of the activation wire of FIG. 6.

A fourth embodiment of the invention is shown in FIGS. 6-7. A first expression of the fourth embodiment of FIGS. 6-7 is for a medical instrument 310 including a tube 312, a distal medical instrument member 313, a medical end effector 314, an activation wire 315, a drive screw 316, a sled 318, and a linkage 320. The tube 312 defines a passageway 321 and has a distal tube portion 322 insertable within a patient. The distal medical instrument member 313 has a proximal end portion 326 pivotally connected to the distal tube portion 322 and has a lumen 327 in communication with the passageway 321. The medical end effector 314 is disposable in the lumen 327 of the distal medical instrument member 313. The activation wire 315 is disposable in the passageway 321 and is connected to the medical end effector 314. The drive screw 316 is positioned in the tube 312 proximal the distal medical instrument member 313. The sled 318 is translatable by rotation of the drive screw 316. The linkage 320 has a first end portion 328 pivotally connected to the sled 318 and has a second end portion 330 pivotally connected to the distal medical instrument member 313 distal the proximal end portion 326 of the distal medical instrument member 313. Rotation of the drive screw 316 translates the sled 318 moving the linkage 320 to articulate the distal medical instrument member 313 with respect to the distal tube portion 322. In one arrangement, the sled 218 has internal threads engaging external threads on the drive screw 216. In one enablement, the tube 212 is a flexible tube.

Examples, without limitation, of medical end effectors 314 of the fourth expression of the embodiment of FIGS. 6-7, include a medical snare (as shown in FIGS. 6-7) and include an electrocautery needle knife (not shown). Other examples are left to the artisan. In one example employing the medical snare, the drive screw 316 is rotated to articulate the distal medical instrument member 313 to a desired orientation, the activation wire 316 is pushed to extend the medical snare out of the distal end of the distal medical instrument member 313 and around patient tissue (such as a polyp), and the activation wire 316 is then pulled to excise the polyp and retract the medical snare (and polyp) into the distal end of the distal medical instrument member 313. In one employment, the activation wire 316 is monolithically connected to the medical end effector 314. Thus, in this employment, the activation wire 316 and the medical end effector 314 are two portions of one continuous piece. In one construction, bearing supports 334 for the drive screw 316 and pivot pins 336 for pivotal connections are provided as shown in FIG. 6, wherein the bearing supports 234 have channels for passage of the activation wire 232. Other constructions are left to the artisan.

In a first extension of any one or more or all of the expressions of the above-described embodiments of the inventions, the medical instrument includes a handle (not shown) connected to a proximal end portion of the tube, wherein the handle has knobs, levers, ports, etc. adapted for manual operation for pulling and/or pushing the cables and activation wires for articulation and activation of the medical instrument. In a second extension, not shown, the proximal end portions of the cables and activation wires are operatively connected to a robotic device for articulation and activation of the medical instrument.

Figure 8:
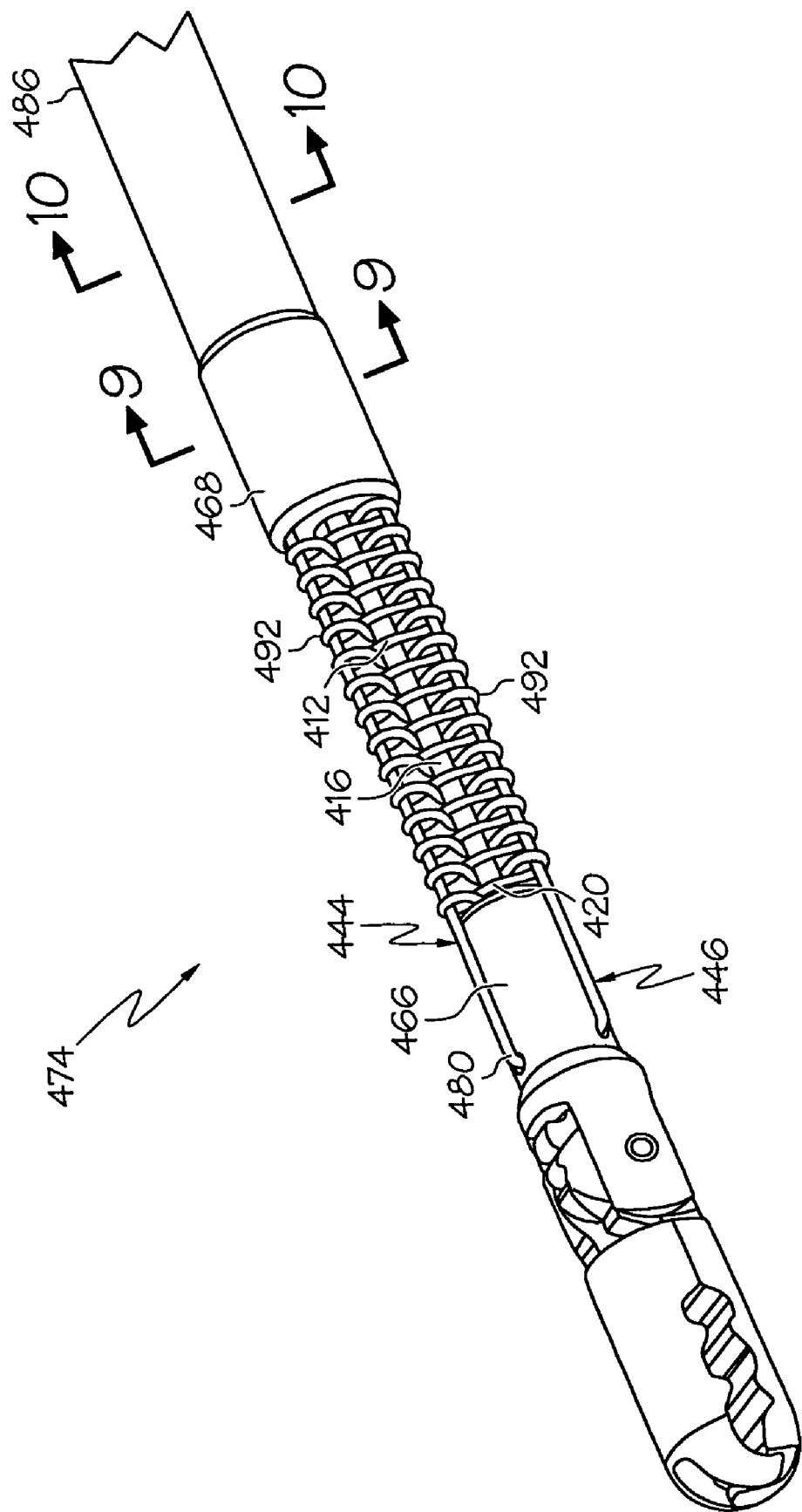
FIG. 8 is a schematic perspective view of a fifth embodiment of the medical instrument of the invention, wherein pulling of at least one cable articulates a distal medical instrument member (such as, but not limited to a medical end effector such as, but not limited to, a medical grasper), and wherein a sheath having lumens extends proximally of a proximal medical instrument member (such as, but not limited to a fitting)
Figure 9:
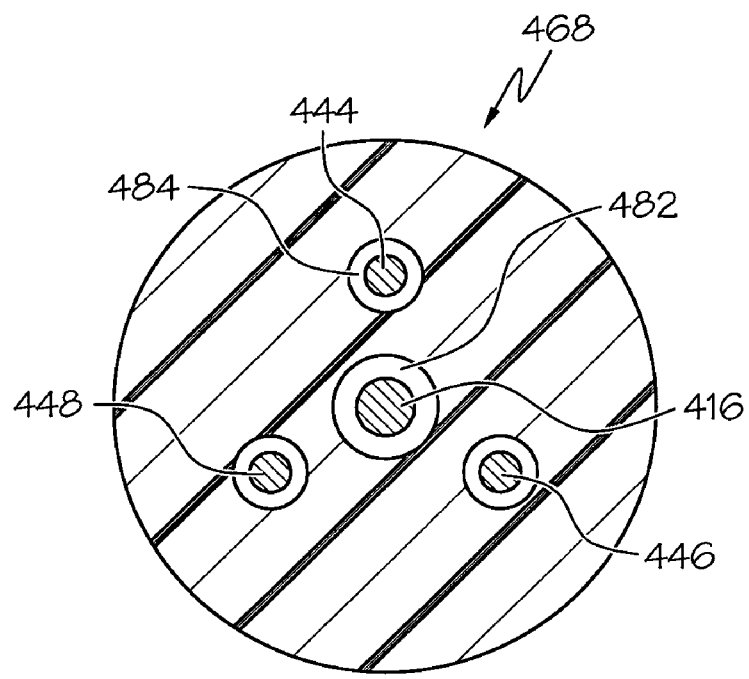
FIG. 9 is a cross sectional view of the proximal medical instrument member of the medical instrument of FIG. 8, taken along lines 9-9 of FIG. 8.
Figure 10:
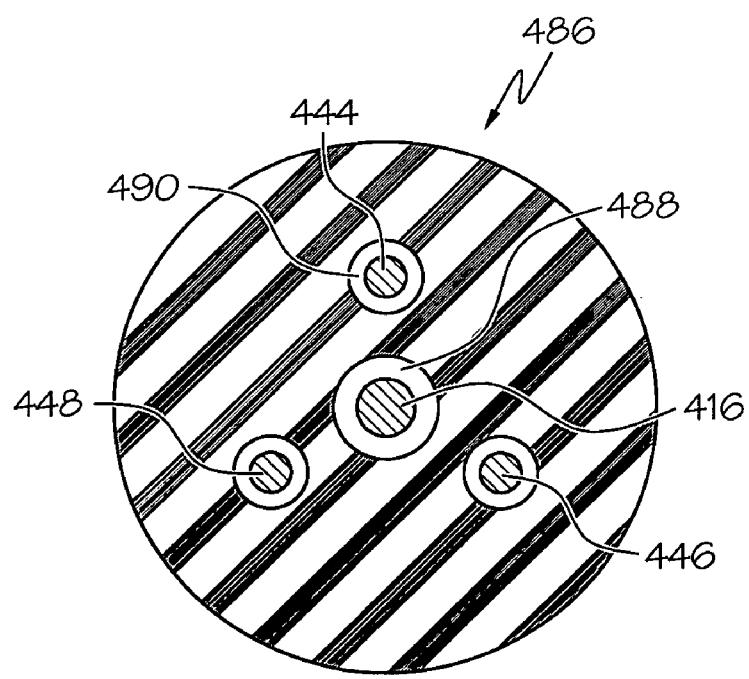
FIG. 10 is a cross sectional view of the sheath of the medical instrument of FIG. 8, taken along lines 10-10 of FIG. 8.

A fifth embodiment of the invention is shown in FIGS. 8-10. A first expression of the embodiment of FIGS. 8-10 is for a medical instrument 474 including a flexible tube 412 (such as, but not limited to, a coil pipe), a distal medical instrument member 466, a flexible medical-end-effector activation wire 416, a proximal medical instrument member 468 (such as, but not limited to, a fitting), and a flexible, lengthwise-translatable first cable 444. The flexible tube 412 has a distal tube portion 420 insertable within a patient. The distal medical instrument member 466 is connected to the distal tube portion 420. The medical-end-effector activation wire 416 is positioned within the tube 412. The proximal medical instrument member 468 is spaced apart from, and is positioned proximal to, the distal medical instrument member 466. The proximal medical instrument member 468 is attached to the tube 412. The lengthwise-translatable first cable 444 is positioned outside the tube 412, is substantially transversely constrained by the proximal medical instrument member 468, and has a first distal cable portion distal cable portion 480 attached to the distal medical instrument member 466. Lengthwise translation of the first cable 444 articulates the distal medical instrument member 466 with respect to the proximal medical instrument member 468.

In an enablement of the first expression of the embodiment of FIGS. 8-10, the proximal medical instrument member 468 has a first lumen 482 surrounding the activation wire 416 and has a second lumen 484 surrounding the first cable 444. In one variation, the medical instrument 474 also includes a flexible sheath 486 attached to, and extending proximally from, the proximal medical instrument member 468 (such as, but not limited to an end cap type of fitting), wherein the sheath 486 has a first lumen 488 surrounding the activation wire 416 and has a second lumen 490 surrounding the first cable 444. In another variation, not shown, the proximal medical instrument member is a stiffer distal end portion of a flexible sheath.

In one modification, the distal medical instrument member 466 is a medical end effector such as, without limitation, a medical grasper as shown in FIG. 8. In one extension, the medical instrument 474 also includes second and third cables 446 and 448 and coil pipes 492 surrounding the cables (only the first and second cables 446 and 448 are shown in FIG. 8) between the distal and proximal medical instrument members 466 and 468. Other examples of medical end effectors are left to the artisan.

Figure 11:
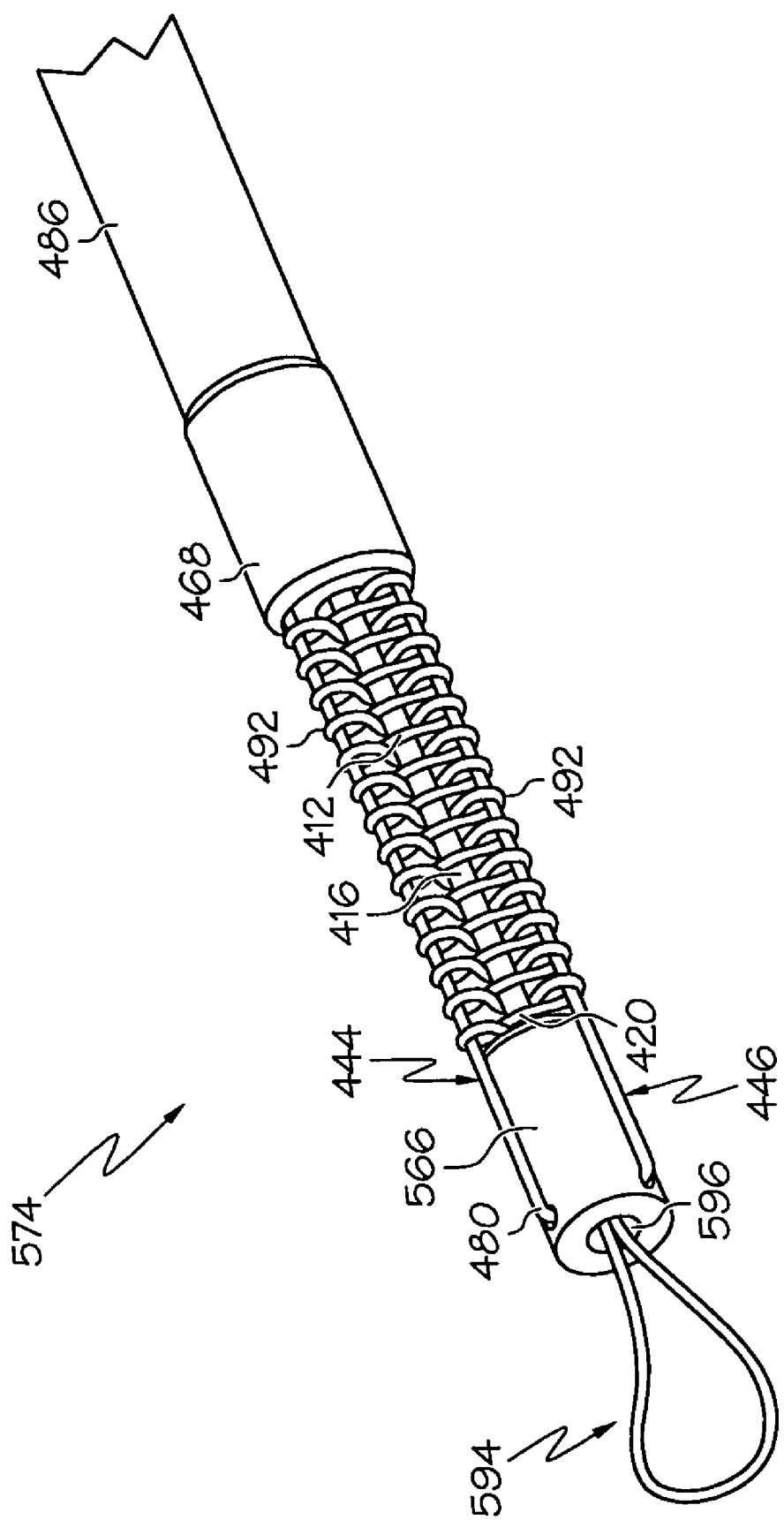
FIG. 11 schematic perspective view of an alternate embodiment of the medical instrument of FIGS. 8-10, wherein pulling of at least one cable articulates a distal medical instrument member (such as, but not limited to, a coupling) which has a lumen in which a medical end effector (such as, but not limited to, a medical snare) is extendable.

In a first alternate modification, shown in the embodiment of FIG. 11, the medical instrument 574, also includes a medical end effector 594, wherein the distal medical instrument member 566 (such as, but not limited to, a coupling) has a lumen 596, and wherein the medical end effector 594 is extendable from the lumen 596 of the distal medical instrument member 566 by translating the activation wire 416. In one example, without limitation, the medical end effector 594 is a medical snare as shown in FIG. 11. Other examples of medical end effectors are left to the artisan.

Several benefits and advantages are obtained from one or more of the expressions of the embodiments of the invention.

In a first example of the first expression of the first, second, third and/or fourth embodiments, the tube is inserted into a working channel of a flexible insertion tube of an endoscope, wherein the medical end effector can be articulated with respect to the insertion tube of the endoscope allowing independent alignment of the wide angle video camera of the endoscope and the medical end effector. In a second example of the first expression of the first, second, third and/or fourth embodiments, the tube has a tube-to-endoscope-rail distal medical instrument member feature allowing the tube to be coupled to, and slid along, an exterior rail of a flexible insertion tube of an endoscope allowing independent alignment of the wide angle video camera of the endoscope and the medical end effector. Non-endoscopic examples are left to those skilled in the art. The cable embodiments allow, with multiple cables, articulation which is not limited to a single plane. The drive screw embodiments allow pivotal articulation unhindered by tube bending from endoscopic insertion within a patient.

While the present invention has been illustrated by a description of several expressions of embodiments, it is not the intention of the applicants to restrict or limit the spirit and scope of the appended claims to such detail. Numerous other variations, changes, and substitutions will occur to those skilled in the art without departing from the scope of the invention. For instance, the medical instrument of the invention has application in robotic assisted surgery taking into account the obvious modifications of such systems, components and methods to be compatible with such a robotic system. It will be understood that the foregoing description is provided by way of example, and that other modifications may occur to those skilled in the art without departing from the scope and spirit of the appended Claims.

What is claimed is:

1. A medical instrument comprising:
   a) a flexible tube having an outermost surface and a distal tube portion insertable within a patient;
   b) a medical end effector connected to the distal tube portion;
   c) a flexible medical-end-effector activation wire disposed within the tube;
   d) a proximal medical instrument member spaced apart from, and disposed proximal to, the medical end effector, wherein the proximal medical instrument member is attached to the tube; and
   e) a flexible, lengthwise-translatable first cable disposed outside of and spaced apart from the outermost surface of the tube between the proximal medical instrument member and the medical end effector, with the flexible, lengthwise-translatable first cable being substantially transversely constrained by the proximal medical instrument member, being substantially transversely unconstrained between the proximal medical instrument member and the medical end effector, and having a distal cable portion attached to the medical end effector, wherein lengthwise translation of the first cable articulates the medical end effector with respect to the proximal medical instrument member.

2. The medical instrument of claim 1, wherein pulling of the first cable articulates the medical end effector with respect to the proximal medical instrument member.

3. The medical instrument of claim 1, also including a flexible first pipe surrounding the first cable and attached to the proximal medical instrument member.

4. The medical instrument of claim 3, wherein the flexible first pipe does not extend distally of the proximal medical instrument member.

5. The medical instrument of claim 3, wherein the flexible first pipe is a first coil pipe, and the tube is a coil-pipe tube.

6. The medical instrument of claim 3, wherein the proximal medical instrument member has a longitudinal axis, and wherein the tube is substantially coaxially aligned with the longitudinal axis within the proximal medical instrument member.

7. The medical instrument of claim 6, wherein the proximal medical instrument member has a longitudinally-extending circumferential surface, and wherein the first pipe is disposed in a surface groove of the circumferential surface of the proximal medical instrument member.

8. The medical instrument of claim 1, wherein the medical end effector has a proximal end-effector portion, and wherein the first cable is attached to the proximal end-effector portion of the medical end effector.

9. The medical instrument of claim 8, wherein the proximal medical instrument member has a first diameter, and wherein the proximal end-effector portion has a second diameter which is substantially equal to the first diameter.

10. The medical instrument of claim 1, also including a flexible, lengthwise-translatable second cable disposed outside of and spaced apart from the outermost surface of the tube between the proximal medical instrument member and the medical end effector, with the flexible, lengthwise-translatable first cable being substantially transversely constrained by the proximal medical instrument member, being substantially transversely unconstrained between the proximal medical instrument member and the medical end effector, and having a distal cable portion attached to the medical end effector, wherein lengthwise translation of the second cable articulates the medical end effector with respect to the proximal medical instrument member.

11. The medical instrument of claim 10, also including a flexible, lengthwise-translatable third cable disposed outside of and spaced apart from the outermost surface of the tube between the proximal medical instrument member and the medical end effector, with the flexible, lengthwise-translatable first cable being substantially transversely constrained by the proximal medical instrument member, being substantially transversely unconstrained between the proximal medical instrument member and the medical end effector, and having a distal cable portion attached to the medical end effector, wherein lengthwise translation of the third cable articulates the medical end effector with respect to the proximal medical instrument member.

12. The medical instrument of claim 11, wherein the medical end effector has a proximal end-effector portion, and wherein the first, second and third cables are attached to the proximal end-effector portion of the medical end effector.

13. The medical instrument of claim 12, wherein the proximal end-effector portion has a circumferential surface, and wherein the first, second and third cables are spaced apart from each other by substantially 120 degrees about the circumferential surface of the proximal end-effector portion.

14. A medical instrument comprising:
   a) a flexible tube having an outermost surface and a distal tube portion insertable within a patient;
   b) a distal medical instrument member connected to the distal tube portion;
   c) a flexible medical-end-effector activation wire disposed within the tube;
   d) a proximal medical instrument member spaced apart from, and disposed proximal to, the distal medical instrument member, wherein the proximal medical instrument member is attached to the tube; and e) a flexible, lengthwise-translatable first cable disposed outside of and spaced apart from the outermost surface of the tube between the proximal medical instrument member and the distal medical instrument member, with the flexible, lengthwise-translatable first cable being substantially transversely constrained by the proximal medical instrument member, being substantially transversely unconstrained between the proximal medical instrument member and the distal medical instrument member, and having a distal cable portion attached to the distal medical instrument member, wherein lengthwise translation of the first cable articulates the distal medical instrument member with respect to the proximal medical instrument member.

15. The medical instrument of claim 14, wherein the proximal medical instrument member has a first lumen surrounding the activation wire and has a second lumen surrounding the first cable.

16. The medical instrument of claim 14, also including a flexible sheath attached to, and extending proximally from, the proximal medical instrument member, wherein the sheath has a first lumen surrounding the activation wire and has a second lumen surrounding the first cable.

17. The medical instrument of claim 16, wherein the distal medical instrument member is a medical end effector.

18. The medical instrument of claim 16, also including a medical end effector, wherein the distal medical instrument member has a lumen, and wherein the medical end effector is extendable from the lumen of the distal medical instrument member by translating the activation wire.

* * * * *